US008118740B2

(12) United States Patent
Howell et al.

(10) Patent No.: US 8,118,740 B2
(45) Date of Patent: Feb. 21, 2012

(54) MOISTURE SENSOR FOR SKIN

(75) Inventors: Thomas A. Howell, Palo Alto, CA (US); Angeline Hadiwidjaja, Los Alto, CA (US); Peter P. Tong, Mountain View, CA (US); C. Douglass Thomas, Campbell, CA (US)

(73) Assignee: IpVenture, Inc., Los Altos, CA (US)

( * ) Notice: Subject to any disclaimer, the term of this patent is extended or adjusted under 35 U.S.C. 154(b) by 1517 days.

(21) Appl. No.: 11/479,665

(22) Filed: Jun. 30, 2006

(65) Prior Publication Data
US 2006/0248946 A1 Nov. 9, 2006

Related U.S. Application Data

(60) Provisional application No. 60/732,925, filed on Nov. 2, 2005, provisional application No. 60/785,825, filed on Mar. 24, 2006.

(51) Int. Cl.
A61B 5/00 (2006.01)
(52) U.S. Cl. .................................................... 600/306
(58) Field of Classification Search .............. 600/306, 600/307
See application file for complete search history.

(56) References Cited

U.S. PATENT DOCUMENTS

| 3,214,278 A | 10/1965 | Mylo |
| 4,513,608 A | 4/1985 | Cuming |
| 4,835,372 A | 5/1989 | Gombrich et al. |
| 4,860,753 A | 8/1989 | Amerena |
| 4,883,063 A | 11/1989 | Bernard et al. |
| 5,014,798 A | 5/1991 | Glynn |
| 5,106,624 A | 4/1992 | Bertini |
| 5,231,993 A | 8/1993 | Haber et al. |
| 5,351,851 A | 10/1994 | Powell |
| 5,353,802 A | 10/1994 | Ollmar |
| 5,394,206 A | 2/1995 | Cocca |
| 5,426,415 A | 6/1995 | Prachar et al. |
| 5,563,584 A | 10/1996 | Rader et al. |
| 5,617,812 A | 4/1997 | Balderson et al. |
| 5,755,672 A | 5/1998 | Arai et al. |
| 5,789,675 A * | 8/1998 | Blaine et al. ................. 73/290 R |
| 5,792,049 A * | 8/1998 | Eppstein et al. .............. 600/306 |
| 5,833,625 A | 11/1998 | Essen-Moller |
| 5,938,593 A * | 8/1999 | Ouellette ...................... 600/300 |

(Continued)

FOREIGN PATENT DOCUMENTS
EP 1 184 663 A3 3/2002
(Continued)

OTHER PUBLICATIONS

"Comparison of a New Test for the Measurement of Resting Whole Saliva with the Draining and the Swab Techniques", Pia López-Jornet et al., Department of Oral Medicine, University of Murcia, Murcia, Spain, electronic publication: Feb. 1997, 6 pages.

"Hydration status measurement by radio frequency absorptiometry in young athletes, a new method and preliminary results," Daniel S. Moran et al., IoP electronic journals, Psysiological Measurement, Feb. 2004, pp. 51-59.

"Sensing device that when implanted in the mouth can detect hydration levels in soldiers", News-Medical.net, Devices/Technology, May 18, 2004, 3 pages.

(Continued)

*Primary Examiner* — Patricia Mallari

(57) ABSTRACT

A moisture sensor for skin is disclosed. With the moisture sensor, a user can determine that her skin is too dry, and can conveniently apply a skin-care product. In addition, in one embodiment, the sensor can assist in identifying different types of skin-care products to apply. As one example, a skin-care product is a type of lotion. As another example, a skin-care product is a type of shampoo.

20 Claims, 16 Drawing Sheets

U.S. PATENT DOCUMENTS

| | | |
|---|---|---|
| 6,017,315 A | 1/2000 | Starr et al. |
| 6,107,537 A | 8/2000 | Elder et al. |
| 6,187,291 B1 | 2/2001 | Weinstein et al. |
| 6,248,067 B1 | 6/2001 | Causey, III et al. |
| 6,251,080 B1 | 6/2001 | Henkin et al. |
| 6,259,654 B1 | 7/2001 | de la Huerga |
| 6,298,990 B1 | 10/2001 | Amrod et al. |
| 6,319,199 B1 | 11/2001 | Sheehan et al. |
| 6,370,426 B1 * | 4/2002 | Campbell et al. ............. 600/547 |
| 6,485,982 B1 | 11/2002 | Charlton |
| 6,529,767 B1 | 3/2003 | Woo et al. |
| 6,569,094 B2 | 5/2003 | Suzuki et al. |
| 6,602,469 B1 | 8/2003 | Maus et al. |
| 6,698,590 B2 | 3/2004 | Moore |
| 6,780,307 B2 | 8/2004 | Kidwell |
| 6,789,936 B1 | 9/2004 | Kraus et al. |
| 6,823,717 B2 | 11/2004 | Porter et al. |
| 6,957,777 B1 | 10/2005 | Huang |
| 7,087,019 B2 * | 8/2006 | Kao ............................. 600/306 |
| 7,323,141 B2 | 1/2008 | Kirchhevel et al. |
| 7,366,675 B1 | 4/2008 | Walker et al. |
| 7,402,135 B2 | 7/2008 | Leveque et al. |
| 2002/0104848 A1 | 8/2002 | Burrows et al. |
| 2002/0111559 A1 | 8/2002 | Kurata et al. |
| 2003/0002238 A1 | 1/2003 | Toyoda |
| 2004/0039255 A1 | 2/2004 | Simonsen et al. |
| 2004/0086456 A1 | 5/2004 | Shirai |
| 2004/0125996 A1 | 7/2004 | Eddowes et al. |
| 2004/0133081 A1 | 7/2004 | Teller et al. |
| 2004/0139048 A1 | 7/2004 | Kerr, II et al. |
| 2004/0171962 A1 * | 9/2004 | Leveque et al. ............... 600/547 |
| 2004/0202685 A1 | 10/2004 | Manzo |
| 2004/0236944 A1 | 11/2004 | Walker et al. |
| 2004/0245205 A1 | 12/2004 | Egli et al. |
| 2004/0257439 A1 | 12/2004 | Shirai et al. |
| 2005/0005678 A1 * | 1/2005 | Duranton ...................... 73/29.02 |
| 2005/0119539 A1 | 6/2005 | Bazin |
| 2005/0119551 A1 | 6/2005 | Maschke |
| 2005/0283203 A1 | 12/2005 | Flaherty et al. |
| 2006/0231109 A1 | 10/2006 | Howell et al. |
| 2006/0241355 A1 | 10/2006 | Howell et al. |
| 2007/0024465 A1 | 2/2007 | Howell et al. |
| 2007/0048224 A1 | 3/2007 | Howell et al. |
| 2007/0213606 A1 * | 9/2007 | Sherman et al. ............. 600/306 |
| 2007/0225578 A1 | 9/2007 | Howell et al. |
| 2007/0249059 A1 | 10/2007 | Stewart |
| 2008/0068559 A1 | 3/2008 | Howell et al. |
| 2008/0146890 A1 | 6/2008 | LeBoeuf et al. |

FOREIGN PATENT DOCUMENTS

| | | |
|---|---|---|
| JP | 01-126535 | 5/1989 |
| JP | 02120652 A | 5/1990 |
| JP | 2001-112741 | 4/2001 |
| JP | 2003028794 A | 1/2003 |
| JP | 2004-236794 | 8/2004 |

OTHER PUBLICATIONS

"Xerostomia Information for dentists, Helping patients with dry mouth", Bartels, Cathy L., http://www.oralcancerfoundation.org/dental/xerostomia.htm, downloaded Mar. 22, 2007, pp. 1-14.

"0136 A new method to measure viscosity in saliva", Becker, K., et al., http://iadr.confex.com/iadr/eur05/techprogram/abstract_67646.htm, downloaded Oct. 14, 2005, pp. 1.

Marketing Devices, http://www.courage-khazaka.de/products/marketing_products.htm, downloaded May 14, 2007, pp. 1-4.

Courage+Khazaka electronic, "Measurement of Skin and Hair at the Point of Sale", Marketing brochure, complete catalogue for skin type analysis devices, http://www.courage-khazaka.de/download/pdf/brochure_marketing_lo.pdf, downloaded Feb. 11, 2008, 17 pages.

Products for Dermatology, http://www.courage-khazaka.de/products/derma_products.htm, downloaded May 14, 2007, pp. 1-4.

Scientific Devices, http://www.courage-khazaka.de/products/scientific_rd_prod.htm, downloaded May 14, 2007, pp. 1-5.

Epidermal "CAPACITANCE", http://www.evicinternational.com/Corneometer.htm, downloaded Dec. 1, 2006, 1 page.

e-pill Pill Bottle Multi Alarm, http://www.epill.com/bottle.html, downloaded Dec. 5, 2006.

GOJO Skin Care Lab, Fast, Effective Hand Cleaning, http://automotive.gojo.com/skin_care/, downloaded Nov. 29, 2006, pp. 1-2.

"L'Oréal and STMicroelectronics applying semiconductors to skin aging," Press Release, Geneva, Oct. 18, 2002, pp. 2.

Moritex USA Incorporated, Sensors & Meters, copyright 2004, http://www.moritexusa.com/products/product_category.php-?plid=5&pcid=10, downloaded Apr. 19, 2006, pp. 1-2.

NELLCOR™ Oximax Sensors™, Tyco Healthcare Group, 2002, pp. 1-5.

Nellcor OxiMax, Sensor Selection Guide, Tyco Healthcare, Oct. 2002, 12 pages.

"NOVA Technology Beams Up the Petite," ATSP Online, http://www.atsp.org/news/supplier.asp?contentID=863&FullStory=, downloaded May 14, 2007, pp. 1-6.

Skin Care and Aging, U.S. National Institutes of Health, National Institute on Aging, last updated Dec. 29, 2005, pp. 1-7.

ViOptix :: Technology, "How ODIS Works," copyright 2006, ViOptix, Inc., http://www.vioptix.com/docs/technology/howitworks.asp, downloaded Nov. 29, 2006, pp. 1-2.

ViOptix, Technology Overview, copyright 2006, VlOptix, Inc., http://www.vioptix.com/docs/technology/technology.asp., downloaded Dec. 5, 2006, pp. 1.

U.S. Appl. No. 11/821,150, filed Jun. 22, 2007.

"Easily check the skin's moisture content," downloaded 2006, pp. 32-33.

Etude, "The Way to skin counseling," Operation Manual, 2005. front cover page and pp. 1-27.

LifePoInt Inc.—Saliva Based Testing Systems for the next generation, LifePoint® IMPACT® Test System, downloaded 2005, 2 pages.

* cited by examiner

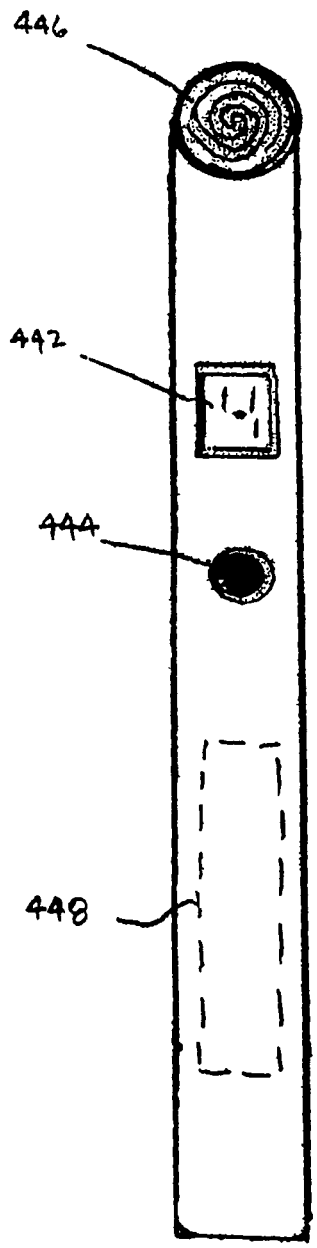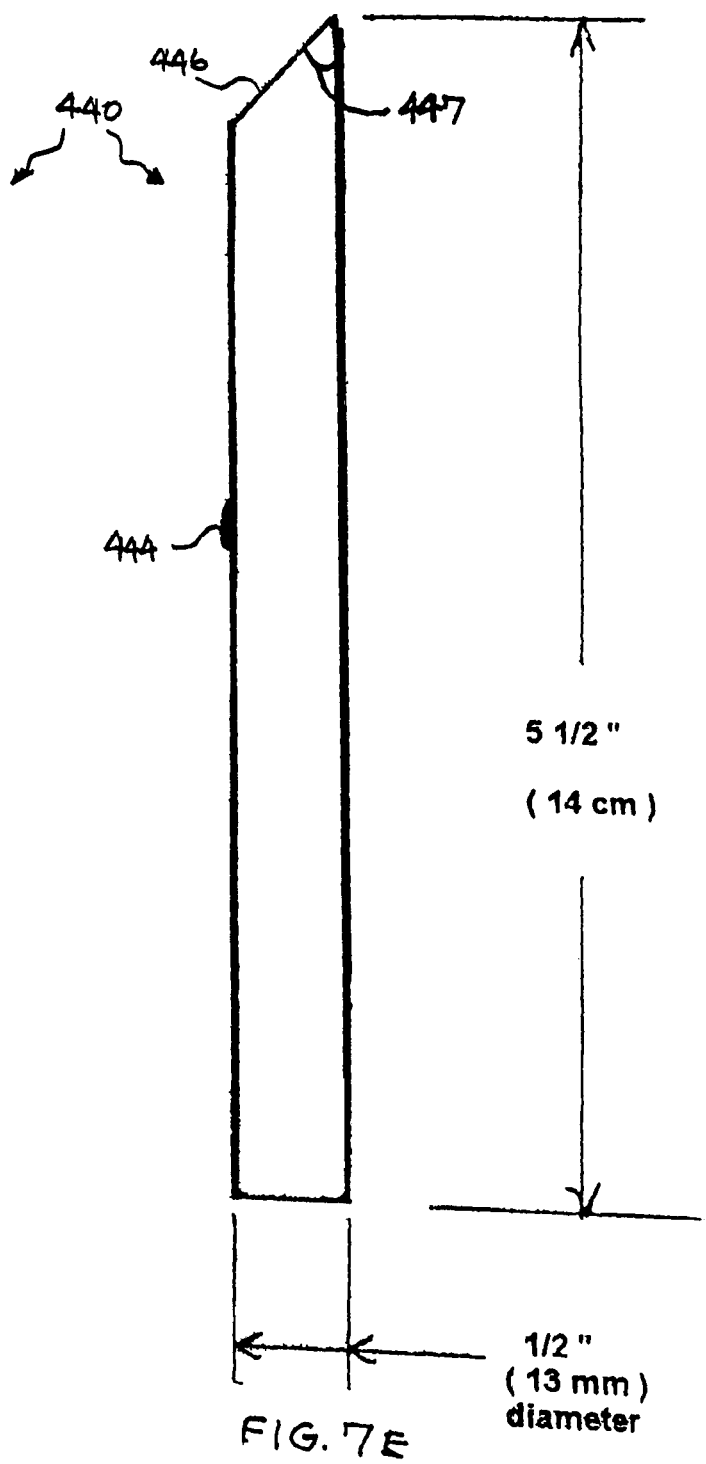
FIG. 7D
FIG. 7E

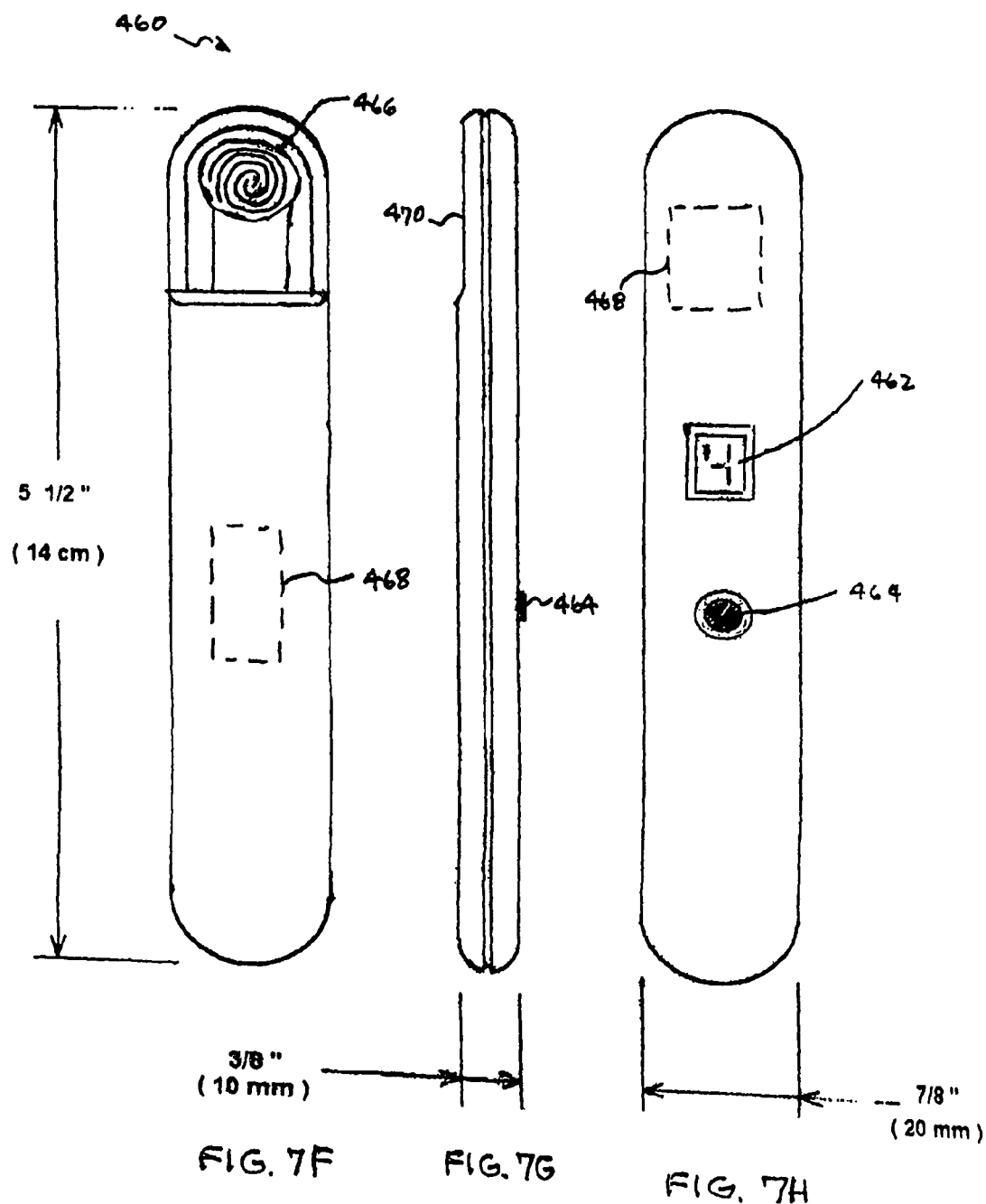

MOISTURE SENSOR FOR SKIN

CROSS-REFERENCE TO RELATED APPLICATIONS

This application is related to U.S. patent application Ser. No. 11/314,545, filed Dec. 20, 2005, and entitled "BOTTLE OF LOTION WITH A SENSOR," which is hereby incorporated herein by reference, which claims priority to each of: (i) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (ii) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (iii) U.S. Provisional Patent Application No. 60/670,957, filed Apr. 13, 2005, entitled "BOTTLE OF LOTION WITH A LOTION SENSOR," and which is hereby incorporated herein by reference; (iv) U.S. Provisional Patent Application No. 60/689,312, filed Jun. 10, 2005, entitled "PERSONAL AND PORTABLE BOTTLE," and which is hereby incorporated herein by reference; and (v) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference.

This application also claims priority to: (i) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference; and (ii) U.S. Provisional Patent Application No. 60/785,825, filed Mar. 24, 2006, entitled "MEDICAL MONITORING SYSTEM," and which is hereby incorporated herein by reference.

FIELD OF THE INVENTION

The present invention relates generally to a moisture sensor.

BACKGROUND OF THE INVENTION

The dryness of a person's skin is typically determined by the person's genetic makeup and the environment. Genetic conditions such as atopic dermatitis and icthyosis cause severe dry skin conditions. According to some studies, just in the United States alone, such genetic conditions affect more than 10 million people. When the skin flares up, it can be very annoying and itchy. One way to alleviate the dry skin conditions is to hydrate the skin, such as by applying lotion and the like. If not quickly treated, the symptoms can rapidly deteriorate.

Skin dryness can also be due to a person's profession. For example, health care professionals have to constantly wash hands. This causes skin dryness.

The aging process might also be linked to skin dryness. Dry skin is susceptible to more wrinkles, which may not be cosmetically appealing.

Sometimes, a person might not even be aware that his skin is dry, or that dry skin has its undesirable consequences.

It should be apparent from the foregoing that there is a need for improved approaches to assist people to be aware of skin dryness. There is also a need to help them to reduce or to avoid skin dryness.

SUMMARY

A number of embodiments of the present invention pertain to a moisture sensor for skin. For example, by use of the moisture sensor, a user can determine that her skin is too dry, and can conveniently apply lotion from a bottle of lotion. The lotion can sooth the skin and reduce problems due to skin dryness, which may result from eczema, cold weather, or constantly washing one's hands. Application of lotion can also help reduce wrinkles by keeping the skin moist. In addition, in one embodiment, the sensor can assist in identifying different types of lotion to apply.

In one embodiment, the moisture sensor can be in the shape of a nail file or a mascara container. In another embodiment, the sensor can be incorporated into other apparatus, such as a pen, a phone or a container (e.g., a lip stick container). The electronics for the sensor could be on one printed circuit board. The circuit board can be flexible so as to more easily conform to the profile of the skin surface to be measured.

In one embodiment, the moisture sensor measures the dryness of a person's scalp, or the skin on the person's head. The sensing surface could be in the configuration of multiple fingers. The fingers could increase the surface area of the sensing surface, while enhancing the ease by which one can measure the scalp underneath a layer of hair. In another embodiment, the sensing surface could be in the configuration of a comb. For example, by using the moisture sensor, a user can determine that he should use a particular type of shampoo or conditioner (e.g., shampoo for dry scalps).

The moisture sensor can be integrated to a bottle of lotion, such as on the bottle's shoulder or cap, or on a face of the bottle. Alternatively, instead of being integrated with the bottle, the sensor can be attachable to the bottle. The sensor can be in a structure that is in the shape of a cylinder, with a corresponding slot on the bottle for the cylinder to be inserted.

In a number of embodiments, a moisture sensor can communicate with one or more electrical components integral with a bottle through wired or wireless connections. The electrical components can provide recommendation to the user based on measured results from the sensor, such as through a display or a speaker on the bottle. In addition, there can be an electrical connector at the bottle for uploading the measured results to another device. For example, the other device can be a memory device or a computer. In another embodiment, the electrical components integral with the bottle are in a base with a slot that allows the bottle to snugly fit therein.

There can be one or more other sensors to measure other attributes of the user and/or the environment. For example, one additional sensor is a humidity sensor to sense the condition of the environment. Such information could further assist a user in determining the type of lotion to apply to her skin.

Other aspects and advantages of the present invention will become apparent from the following detailed description, which, when taken in conjunction with the accompanying drawings, illustrates by way of example the principles of the invention.

BRIEF DESCRIPTION OF THE DRAWINGS

FIGS. 7D and 7E are front and side view for a moisture sensor according to still another embodiment of the invention.

FIGS. 7F, 7G and 7H are rear, side and front view for a moisture sensor according to still another embodiment of the invention.

Same numerals in FIGS. 1-10 are assigned to similar elements in all the figures. Embodiments of the invention are discussed below with reference to FIGS. 1-10. However, those skilled in the art will readily appreciate that the detailed description given herein with respect to these figures is for explanatory purposes as the invention extends beyond these limited embodiments.

DETAILED DESCRIPTION

Figure 1A:
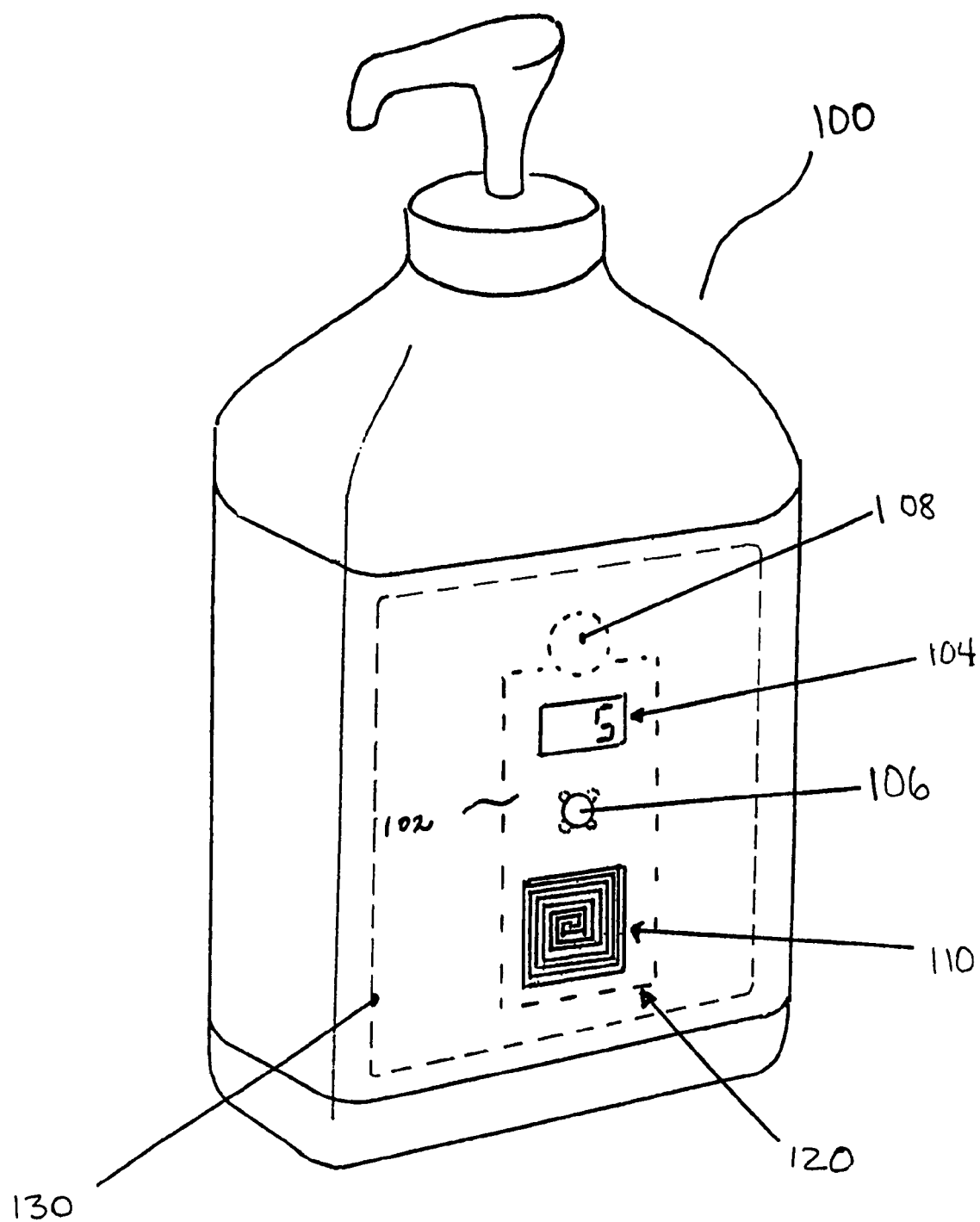
FIG. 1A shows a bottle of lotion with a moisture sensor according to one embodiment of the invention.

FIG. 1A shows a bottle of lotion 100 with a moisture sensor 102 according to one embodiment. The sensor 102 is integral with or integrated into the bottle. The sensor 102 can provide an indication regarding the dryness of a user's skin, and can provide a recommendation or suggestion regarding the application of lotion, such as whether the user should apply lotion.

Figure 1B:
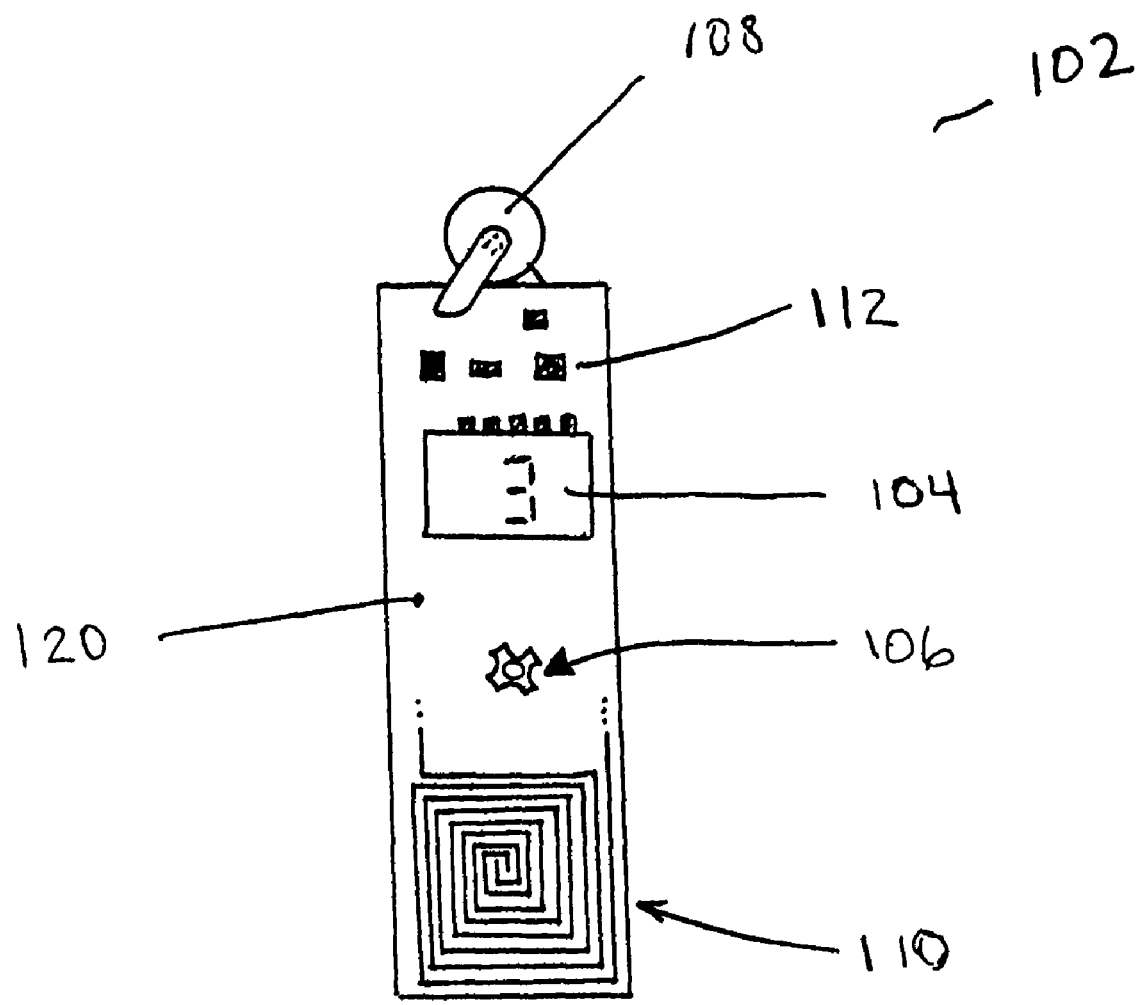
FIG. 1B shows a number of electrical components on a printed circuit board of a moisture sensor according to one embodiment of the invention.

FIG. 1B shows a printed circuit board 120 with a number of electrical components for the moisture sensor 102 according to one embodiment. The printed circuit board can be a rigid or a flexible printed circuit board. The electrical components include a display 104, such as a LCD display, an on/off switch 106, a sensor head 110, and one or more integrated circuits 112, with one being an electronic controller. The controller is configured to control operations of the electronics on the printed circuit, such as the display 104. Another electrical component for the sensor 102 is a power source, such as a battery 108, which, in one embodiment, is a coin battery. In one embodiment, a sensor head 110 is the part of the sensor 102 that touches and measures the substance or the area to be sensed. The switch 106 can be a dome switch. If a user wants to take a measurement, the user pushes the switch. This will turn on the sensor 102 to measure skin dryness. Outputs from the measurements are shown on the display 104. In one embodiment, the sensor 102 is used with the bottle of lotion 100. The sensor 102 is an apparatus that provides an indication regarding the dryness of the user's skin. In one approach, the sensor 102 uses capacitive effect to determine dryness.

In one embodiment, the sensor 102 is referred to herein as a moisture sensor and it is used in conjunction with a bottle of lotion 100 to assist the user of the bottle in determining whether lotion from the bottle should be applied to the user's skin. In another embodiment, the sensor 102 is referred to herein as a moisture sensor and it helps the user determine whether the user's skin needs lotion, though the sensor may not be used together with a bottle of lotion.

Figure 1C:
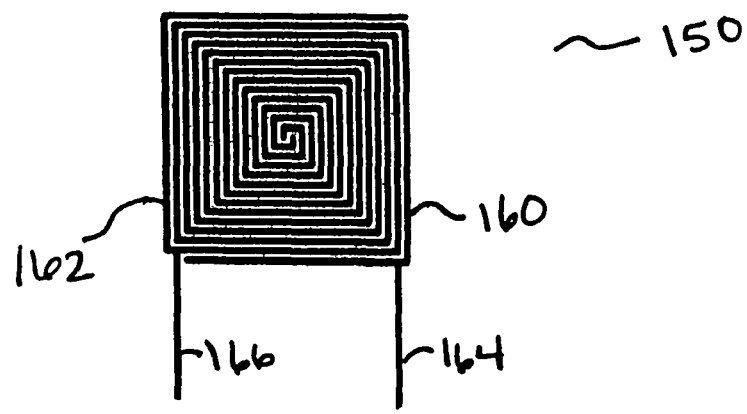
FIG. 1C shows different embodiments of electrical circuits for a moisture sensor head according to the invention.
Figure 1C:
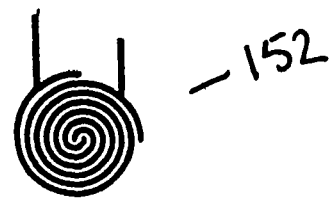
Figure 1C:
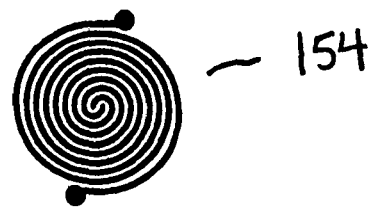
Figure 1C:
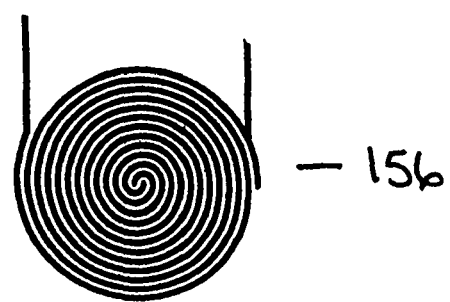

FIG. 1C shows different embodiments 150, 152, 154 and 156, of electrical circuits for a moisture sensor head 110 that uses closely-spaced electrically conducting lines. One of the embodiments, 150, is rectangular in shape, and the other three are circular or spiral in shape. They can be made by printing conducting lines on a printed circuit board. The conducting lines are typically covered by a thin layer of electrically insulating material. An example of such a layer of insulating material is a solder mask, a material commonly used in the circuit board industry. Each of the embodiments shown in FIG. 1C includes two conducting lines adjacent to each other and intertwined together, for example, in the shape of spirals. In one embodiment, the conductors are 10 mils wide, with 10 mils spacing between the lines. Using the rectangular embodiment, 150, as an example, one can see the two conductors 160 and 162. Each of the conductors is connected to a lead, the conductor 160 to the lead 164, and the conductor 162 to the lead 166. The sensor 102 (e.g., sensor body) measures the capacitance between the two conductors through the two leads. The capacitance depends on the dielectric constant of the materials adjoining the conductors. With the sensor head 110 pressed against a piece of skin, the dielectric constant changes depending on the skin's moisture content. Different techniques are known in the art to measure capacitance, and will not be further described.

As an example, with the square embodiment 150, if it is not touching any skin, the capacitance measured can be about 0.04 nF (nano-farads). When the sensor head is touching a dry skin, the capacitance measured can be about 0.09 nF, and when the sensor is touching a moist skin, the capacitance measured can be about 0.15 nF.

In the example shown in FIG. 1A, the sensor head 110 is closer to the bottom of the bottle than the display 104. In another example, the printed circuit board 120 is switched 180 degrees, with the display 104 being closer to the bottom of the bottle. In yet another embodiment, with the printed circuit board being a flexible printed circuit board, the printed circuit board does not have to be on a flat surface of the bottle. The printed circuit board could be on a curved surface of the bottle, and the bottle could have more curvature.

Figure 2:
FIG. 2 illustrates a person using a moisture sensor on a lotion bottle according to one embodiment of the invention.

FIG. 2 illustrates an example of a person using a moisture sensor on a lotion bottle according to one embodiment. The person turns on the sensor, and then presses the sensor head against her face to get a measurement. In one embodiment, the sensor tracks the measurements until changes in the measurements are within a preset threshold. Then the sensor takes that measurement as the final measurement.

In one embodiment, there is an indentation on the bottle surface to hold the printed circuit board 120 with the battery 108 so that the surface of the board is substantially flush with the outer surface of the bottle.

In the embodiment shown in FIG. 1A, the sensor 102 includes a battery 108. In another embodiment, the sensor can be powered by a fuel cell or a solar cell. In yet another embodiment, the bottle includes a latch or a door, to allow the power source, such as the battery, to be accessed (e.g., battery replaced).

In one embodiment, the sensor is water-sealed because the sensor might get wet or there could be moisture on the surface of the sensor. One way to seal the electrical traces on the printed circuit board 120 is by covering them with solder mask. Other mechanisms of sealing the electrical traces include, for example, epoxy and adhesive tape.

There can be one or more labels 130 on the bottle 100. In one embodiment as shown in FIG. 1A, one can place the printed circuit board on the front surface of the bottle 100 and then place a label 130 over it. In one embodiment, the label 130 has at least three openings, one for the switch 106, one for the display 104, with the third for the sensor head 110. The sensor head 110 can be covered or encapsulated by solder mask or other type of insulating film. The label 130 can provide improved aesthetic appearance and/or serve to secure the moisture sensor to the bottle. The label could be a shrink-wrap on the surface of the bottle. The shrink-wrapping could be made of a piece of plastic material. Also, there could be, for example, a company logo and/or advertisement on the label 130.

Figure 3:
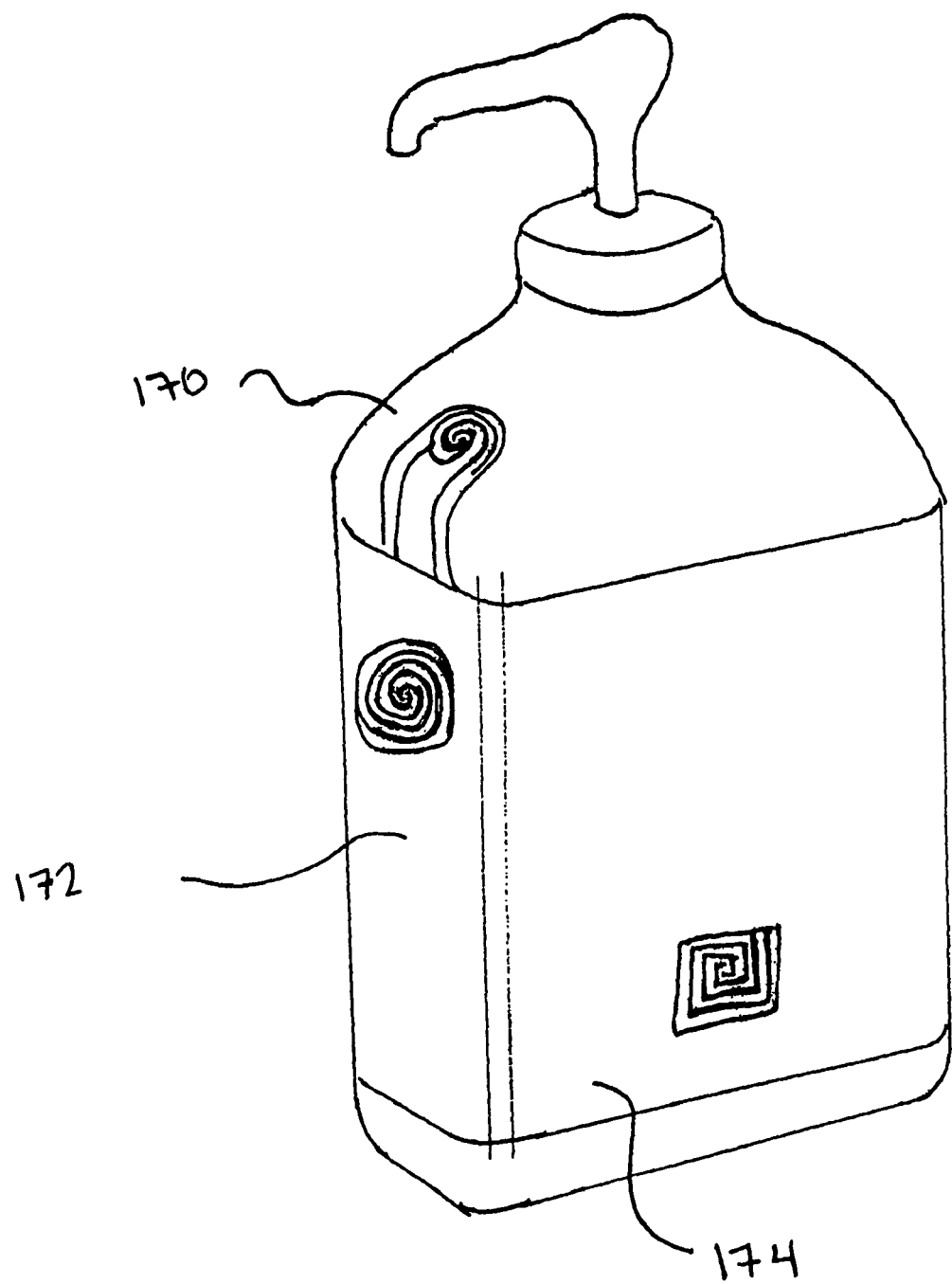
FIG. 3 shows different embodiments regarding the locations of a moisture sensor head that is integral with a bottle of lotion according to the invention.

FIG. 3 shows different embodiments of the locations of a moisture sensor head that is integral with a bottle of lotion. For example, the sensor head can be integrated on a shoulder 170, on a side surface 172, or on a front surface 174 of the bottle. FIG. 1A shows the sensor also on a front surface of a bottle.

Instead of being integral with a bottle, in one embodiment, a moisture sensor is detachable from and can be attachable to the bottle. In one embodiment, the bottle can further include, for example, a clip, a band, a piece of string or a cord that can serve to attach the sensor to the bottle. In another embodiment, instead of the bottle, the sensor includes, for example, a clip, band, string or cord that can serve to attach the sensor to the bottle.

Figure 4A:
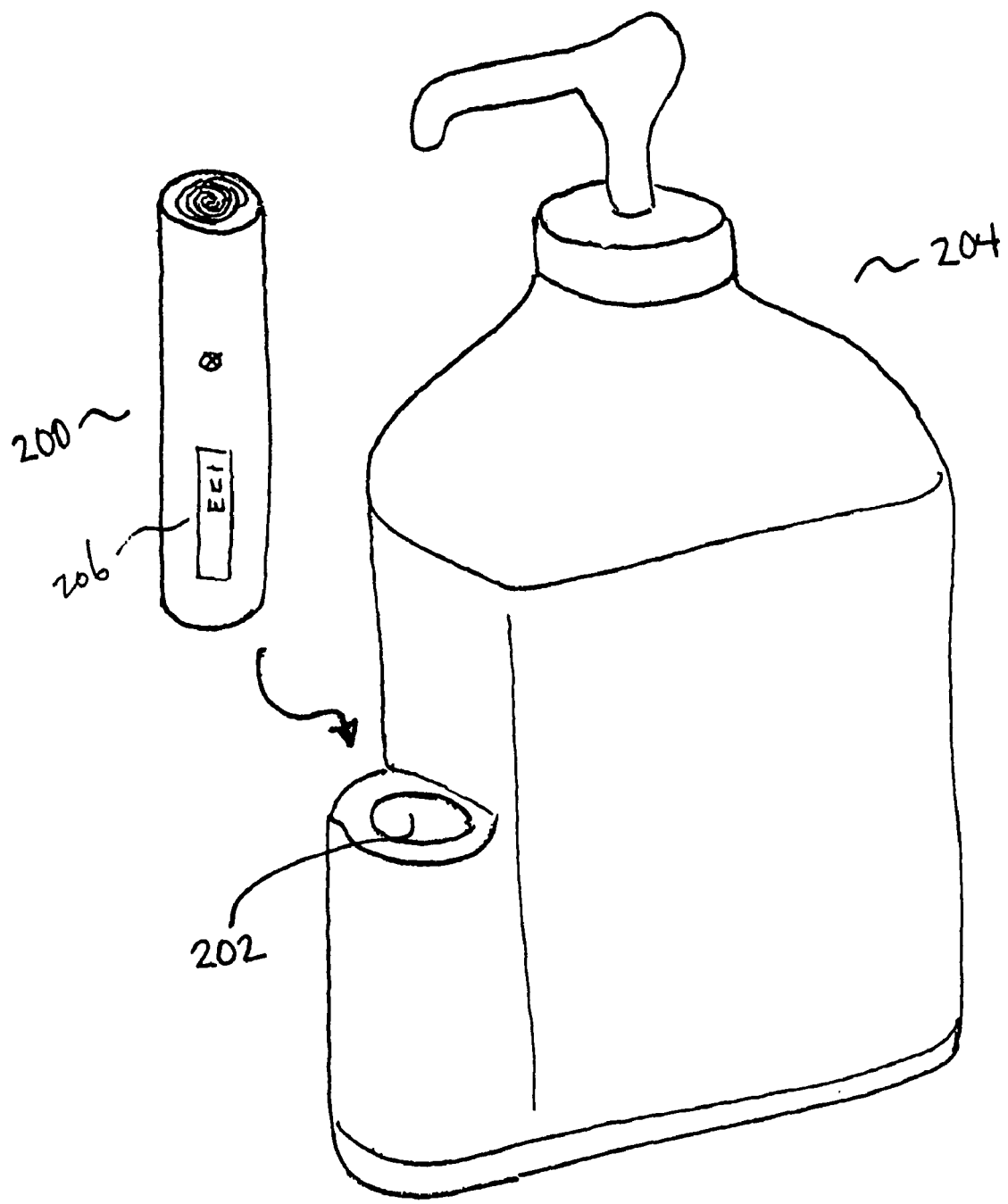
FIGS. 4A-4B show different embodiments of a bottle of lotion with a detachable moisture sensor according to the invention.
Figure 4B:
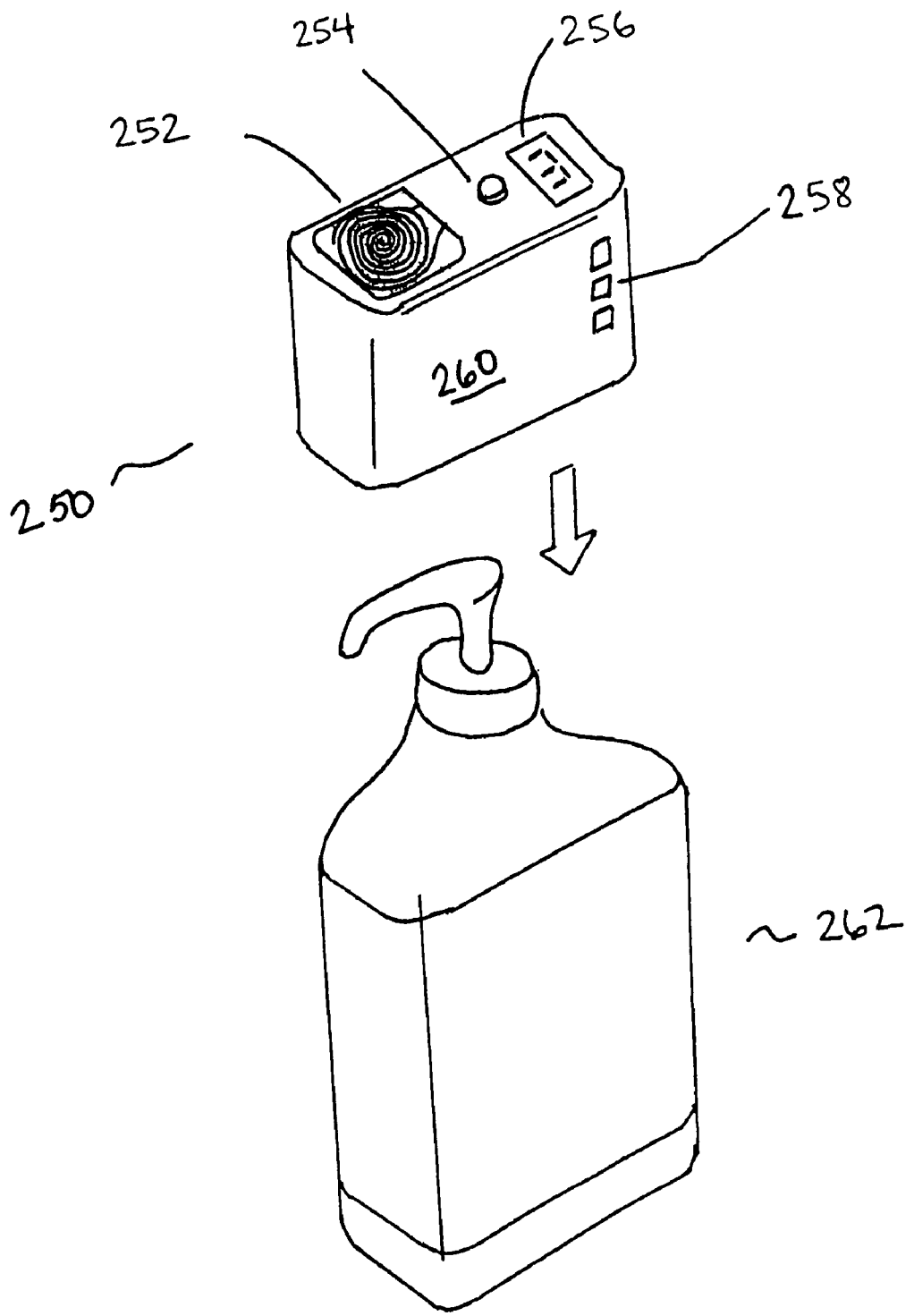

Different embodiments of a sensor that is detachable and attachable are shown in FIGS. 4A and 4B. In FIG. 4A, an attachable sensor 200 can be in a structure that is in the shape of a tube, such as a cylindrical tube. There can be a slot or a cavity 202 on the side of the bottle 204 to receive the tube 200. The sensor 200 can be inserted into the slot 202 when not in use.

FIG. 4B shows another embodiment of a detachable sensor 250. The sensor 250 is part of a cap 260 of the lotion bottle 262. The sensor 250 includes a sensor head 252, an on/off switch 254, and a display 256. In this example, the sensor 250 can also include an electrical input/output port 258, which will be further described below. Note that the sensor in the embodiment shown in FIG. 4B can also be described as being integrated with the bottle if the cap 250 is considered to be a part of the bottle. The electrical port 258 can, in one embodiment, be an electrical connector.

In yet another embodiment, though detachable from the bottle, a moisture sensor is tethered to the bottle. For example, the sensor includes a sensor head that is fabricated on a circular disk. The disk is connected to the bottle through a wire that can be extended from and retractable back into an opening of the bottle. The wire can be rigid or flexible. The sensor head is electrically coupled to at least one electrical component integral with or attached to the bottle through the extendable and retractable wire. In one embodiment, the at least one electrical component can be, for example, a display, an electrical switch, an integrated circuit, a resistor, a capacitor, an inductor, a battery or a speaker.

In the embodiments shown in FIG. 4A and 4B, the sensor includes a display, such as the sensor 200 shown in FIG. 4A includes the display 206. In another embodiment, a detachable sensor includes a sensor head, but does not include an output device, such as a display. For example, the detachable sensor shown in FIG. 4A does not include the display 206. Instead, there can be one or more electrical components integral with or attached to the bottle, with one of the components being an output device, such as a display. The one or more electrical components integral with or attached to the bottle are electrically coupled to the detachable sensor.

In different embodiments, a detachable sensor can wired or wirelessly communicate with one or more electrical components in a corresponding bottle. In the embodiment that the sensor is tethered to the bottle, the sensor can communicate with the bottle's electrical components by a wired connection through the tether.

On the embodiment that the sensor is not tethered to the bottle, the sensor can communicate with the bottle's electrical components wirelessly. The communication protocol can be based on Bluetooth® or Zigbee® standards.

In yet another embodiment, for the sensor that is not tethered to the bottle, the sensor electrically communicates with the bottle when the sensor is inserted back into or received by a slot, a receptacle or a housing at the bottle. Data can be temporarily stored at the sensor until the sensor is received by the receptacle at the bottle. Then the data is transferred to the bottle.

In one embodiment, the sensor head includes an application surface, which is the surface configured to touch the skin for measurement. In one embodiment, the application surface of the sensor head is not flat. For example, it can have a curved surface, such as a concave surface. In another embodiment, the application surface of the sensor head conforms to the area where dryness is being measured. In one embodiment, the sensor head is flexible to conform to the shape of the area to be measured. This flexibility could be achieved by the printed circuit board being flexible, such as based on a type of polyimide material known as Kapton®.

In yet another embodiment, a substantially constant force is maintained when the sensor head is applied or pressed onto the surface to be measured. For example, if the sensor includes a printed circuit board inside a housing, the constant-force mechanism can be achieved, such as by placing a soft spring or a piece of foam between the back of the circuit board and the sensor head housing. When the sensor head is pressed onto the surface to be measured, the soft spring or the piece of foam maintains a substantially constant force onto the surface.

Figure 5:
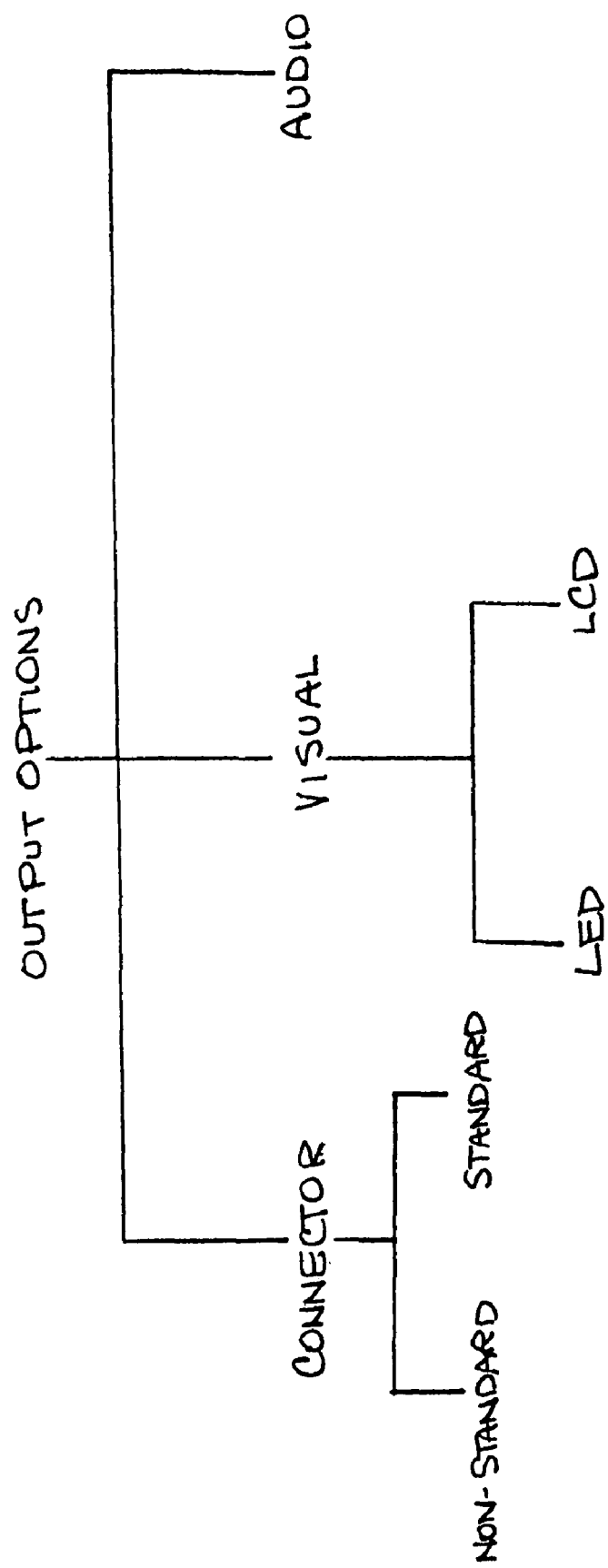
FIG. 5 shows different embodiments of output options from a bottle of lotion with a moisture sensor according to the invention.

FIG. 5 shows different embodiments of output options from a bottle of lotion with a moisture sensor. The electrical components for each of the options can be in a detachable sensor, or integral with or attached to a bottle, or partially in a detachable sensor and partially integral with or attached to a bottle.

Figure 6:
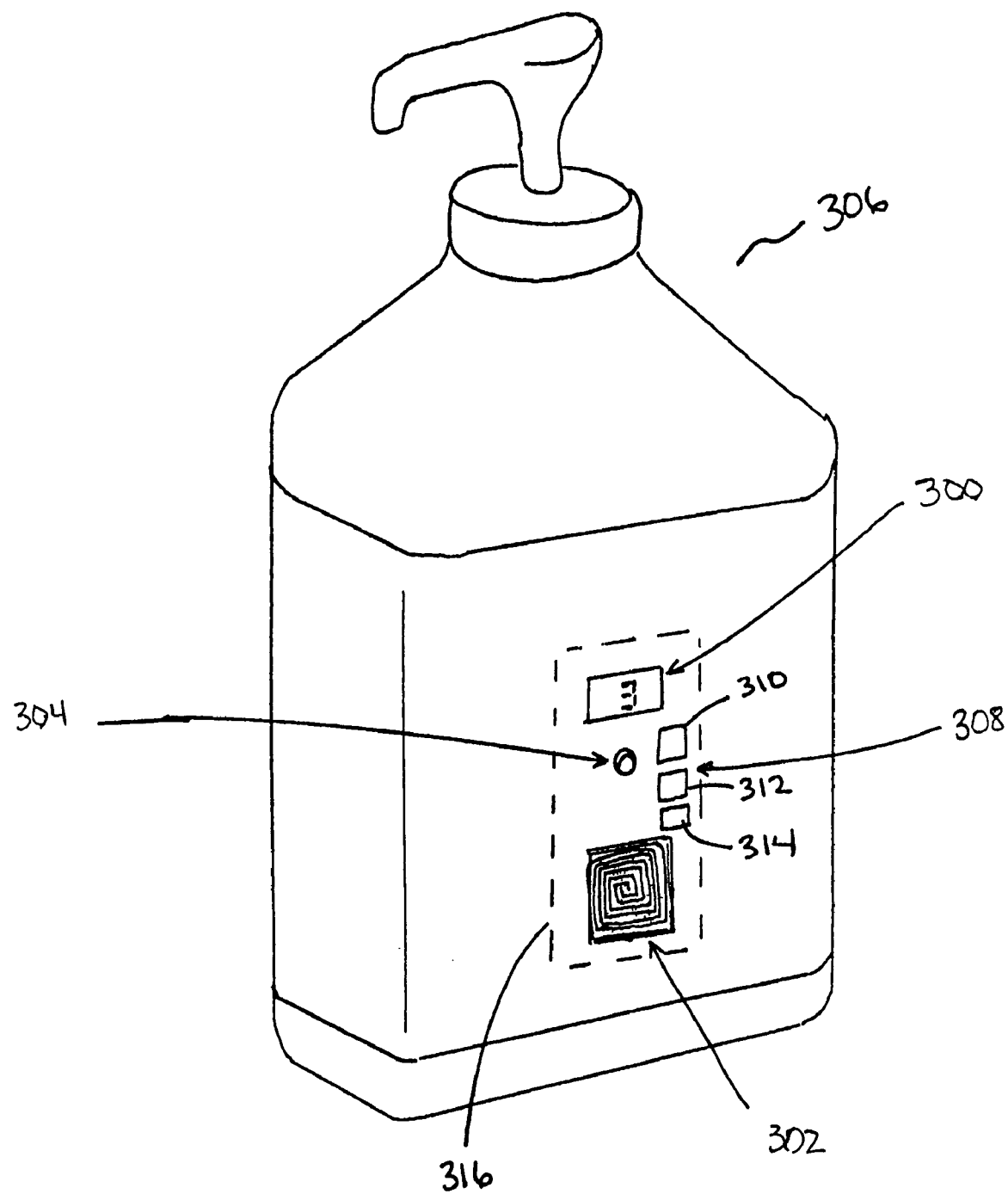
FIG. 6 shows a data output port on a lotion bottle according to one embodiment of the invention.

In one embodiment, the output option includes an electrical connector. The connector can be in the bottle as shown, for example, in FIG. 6. In FIG. 6, the bottle 306 includes a display 300, a sensor head 302 and an on/off switch 304. In this embodiment, the bottle 306 also includes an electrical port 308. The port can be a data port with three conductive pads or dots, 310, 312 and 314, on a circuit board 316. These three conductive pads could correspond to Tx, Rx and ground, as commonly used in a standard serial data port. One can make connections to electrical components in the bottle through the three pads with a corresponding mating connector, which is not shown in the figure.

In another embodiment, the electrical port is a connector, and the connector is a standard connector, such as a USB connector.

The electrical port can be used to couple an external device to electrical components integral with or attached to the bottle. For example, the electrical port can be used to upload the measured data by a moisture sensor to another device, such as a memory device, like a flash memory card. Then, the memory device can be removed and later attached to another computing instrument to upload the measured data into that instrument.

Instead of at the bottle, in one embodiment, an electrical port is part of a moisture sensor, such as for a standalone moisture sensor that is separate from or not integral with a bottle of lotion.

In another embodiment, an output option is visual, and can be based on LED, LCD, electric ink or thermochromic ink technologies. The output can be a relatively simple indicator. For example, the output can be based on color, such as red, yellow and green. Red can mean that the person's skin is very dry, with green meaning sufficiently moist and yellow being in between. In another example, the output can be either affirmative or negative. For example, the output from a LCD display is a specific type of symbol, such as a bottle with or without a slash. One type of symbol indicates that the user should apply lotion, and the other indicating that the user does not need to apply lotion.

In another embodiment, the visual output can be more elaborate. It can be a message. The message can be a recommendation for the type of lotion to apply based on the measurements. Depending on the dryness of the skin, the recommendation can be changed accordingly based on sensor measurement. For example, a lotion company can have a range of lotions, such as from very creamy (or more oily) to not that creamy (or less oily). The lotion company can designate a number of levels, such as five, for the range, with each level corresponding to a type of lotion along the range of lotions. For example, level 1 will correspond to very creamy lotion. If the sensor measurement indicates that the person's skin is very dry, the dryness would be equated to level 1. Then the recommendation for the user would be to use the very creamy lotion from the company.

To tailor a type of lotion for a person, in one embodiment, a moisture sensor measures the skin of the person for a duration of time, typically in a periodic manner. Based on the measurements, a specific type of lotion is recommended to the person. This recommendation can be provided by a message on the display of the bottle. In another embodiment, the measurements are transmitted to a computer, either through a wired connection or wirelessly. The computer then provides the recommendation. Due to changes in weather, the person might need different types of lotion at different times of the year. In yet another embodiment, the bottle can alert the person to periodically perform the measurements, such as every three months.

In another embodiment, the message on a display can be used to promote products for a company. For example, the products being promoted can be related to skin care.

The time when a promotion is shown on the display can be set by a number of ways. For example, with a bottle having an on/off switch and a display, one can push the switch if one wants to make a measurement. After the measurement, the person can turn the bottle off or it can automatically turn off. In one embodiment, an advertisement or promotion would be shown on the display if the switch is turned off. In another embodiment, the display will show advertisement if the measured results by the sensor have not changed for a predetermined amount of time, such as 30 minutes. In other words, when no one is making any measurements, such as no one pushes the switch on the bottle, the display can show one or more different products from a company. In yet another embodiment, after the measurement, the person can turn off the bottle. Then, after a duration of time, such as 30 minutes, if no one pushes the switch, the bottle will automatically turn on its display to show advertisements.

Alternatively, to manage power consumption, the bottle can display advertisements for a period of time after the bottle is used. For example, the bottle would be considered used if moved or if the start button is pressed. A motion sensor can be integral with or attached to the bottle to detect bottle motion. A motion sensor might also detect motion of a person in the vicinity of the bottle and, in view of such motion, a display on the bottle can be activated (e.g., to display an advertisement).

The advertisement can be from the manufacturer, the wholesaler, the retailer or the distributor of a bottle of lotion. The promotion can be on a product. A product can be a service. The product can be related to skin care, such as lotion.

In one embodiment, the product being promoted can change. This change can be based on time. For example, every week the display can change the product shown, such as the display showing a type of soap on one week and automatically changing to a type of shampoo the next week. The type of soap being promoted can be more suitable for the corresponding skin type as indicated by the lotion, or as indicated by measurements from a moisture sensor.

In one embodiment, the information shown on the display can be modified based on materials transmitted from a company to the bottle. For example, the bottle can also include a connector. When the user uses his computer to visit the website of the company, the user is encouraged to hook up the connector to his computer. The company gives incentives to the user if the user is willing to allow the company to download company information onto the bottle.

To illustrate, for example, the company has a webpage. Through the page, the company tells the user that the user can get a discount for their products if the user allows the company to download information into the lotion bottle. The discount can be on the products that the company is going to download information to the bottle. If the user agrees, the user can select an icon or a button on the webpage. Once the user has selected that button, the webpage will signal the user to connect the bottle to the computer. Then, the webpage will transfer a file to the computer to be downloaded to the bottle. The user can then be allowed to retrieve the discount coupons from the website and can print out the coupons on his printer.

In another embodiment, instead of visual outputs, as shown in FIG. 5, the output option is audio, such as through a speaker. For example, the speaker can provide a beep at a regular interval to remind the user that it is about time to apply lotion or check her skin using the sensor. As another example, the audio output can also provide information about the associated product or related products.

In one embodiment, after the sensor starts measuring, such as when the sensor head is pressed onto a surface, an audio output, such as a beep, provides an indication that the measurement is done. This could be achieved when the output from the sensor does not fluctuate beyond a certain threshold, such as when the change in percentage from an output to its immediate next output is below a preset amount. In another embodiment, if the sensor determines that the user's skin is a bit too dry or the user needs lotion, the sensor would produce an audio output, which could be a pre-stored message, such as, "You need lotion."

In another embodiment, the sensor starts measuring when the sensor head is pressed onto a surface. This can be done, for example, by having a pressure sensor or a switch at the sensor head. The pressure sensor or switch gets activated when pressed. The moisture sensor then continues to measure for a preset amount of time, such as 1.5 seconds. After the preset amount of time, the moisture sensor stops measuring. In one approach, the largest value (e.g. capacitance value) measured during the preset amount of time is chosen to be the measured value.

Instead of using a pressure sensor, other mechanisms can be used to automatically activate the moisture sensor. For example, there can be a switch with a spring. When the force exerted on the spring exceeds a certain amount, such as 4 ounces, the switch would turn on and the moisture sensor would take a measurement. In another embodiment, the moisture sensor includes a motion detector. If the motion detector senses motion, the moisture sensor would be automatically activated to take measurements for a preset amount of time.

A number of embodiments have been described where a moisture sensor is integral with or attached to a bottle. In one embodiment, the moisture sensor is a stand-alone sensor. It can be handheld or portable, and can be sold or acquired apart or separately from the bottle. Different electrical features/capabilities described above regarding a bottle can also be implemented into the handheld or portable moisture sensor according to different embodiments.

Figure 7A:
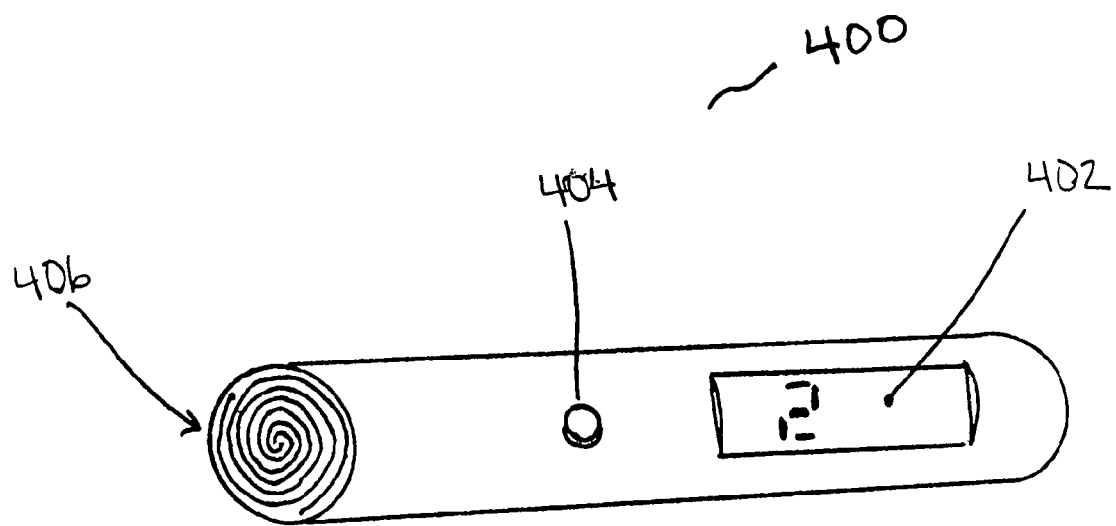
FIG. 7A shows a moisture sensor according to one embodiment of the invention.

FIG. 7A is a perspective view of a moisture sensor 400 according to one embodiment of the invention. The general configuration of the sensor is cylindrical. The sensor 400 also includes a display or screen 402, an on/off switch 404, and a sensor head 406. In one embodiment, the sensor head 406 includes an application surface. The application surface can include two conducting lines adjacent to each other, with the conducting lines covered by a thin insulating film. In FIG. 7A, the display can be a flat display located in a recessed and flat surface. In another embodiment, the display can be a flexible display, such as an electrophoretic display. In yet another embodiment, the general configuration of the sensor is rectangular, or the sensor has a rectangular cross section. In the embodiment shown in FIG. 7A, the application surface can be substantially perpendicular to the display 402. In one embodiment, the sensor head is on a printed circuit board, which is electrically coupled to one or more other printed circuit boards in the sensor. In another embodiment, the sensor just has one printed circuit board and it is a flexible printed circuit board. In the embodiment shown in FIG. 7A, the flexible board can be bent so that a portion of it is for the sensor head, and another portion is for other electrical components, such as for coupling to the display 402.

Figures 7B, 7C:
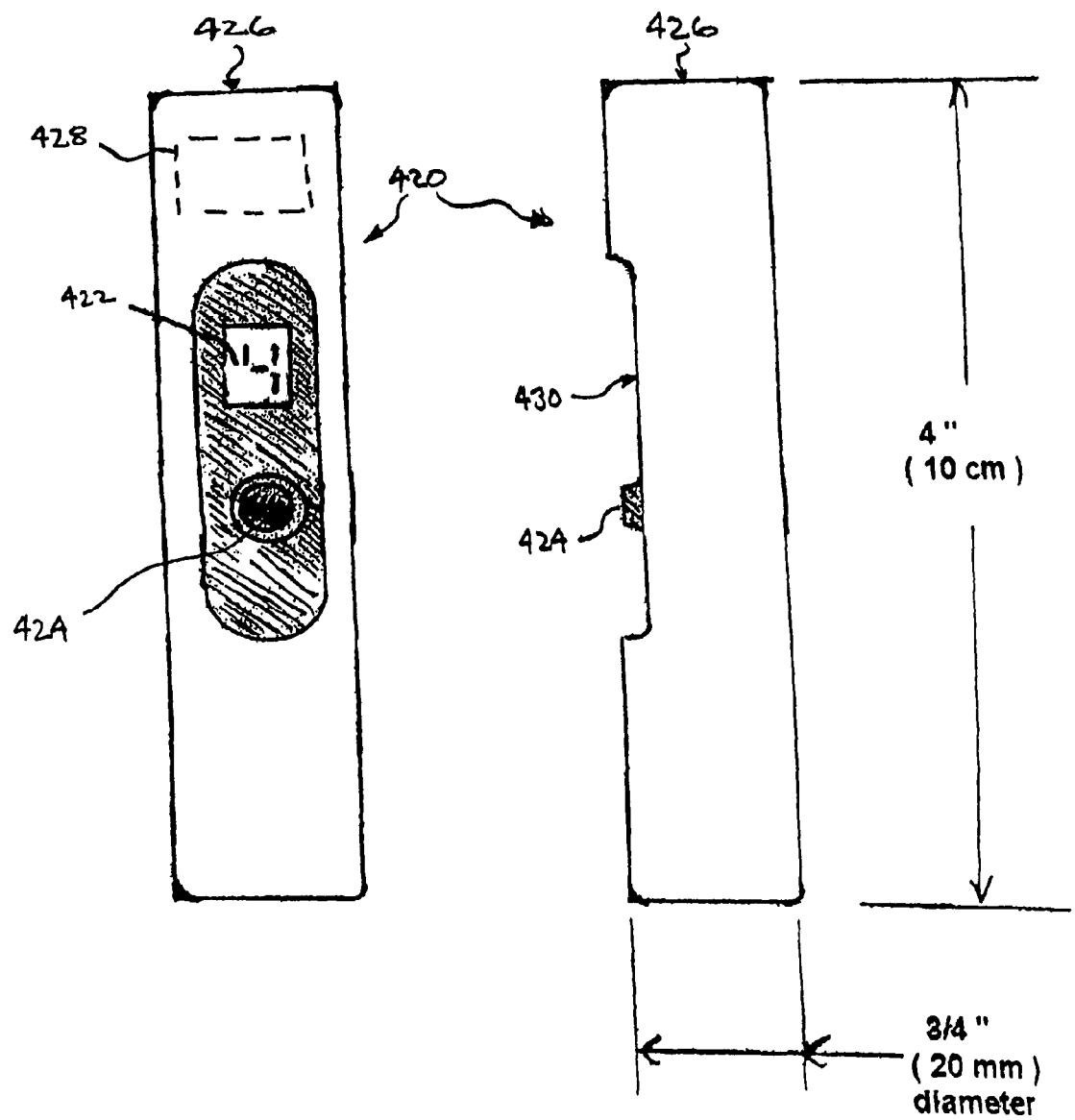
FIGS. 7B and 7C are front and side view for a moisture sensor according to another embodiment of the invention.

FIGS. 7B and 7C are front and side views for a moisture sensor 420 according to another embodiment of the invention. The sensor 420 also includes a display or screen 422, an on/off switch 424, and a sensor head 426. In this embodiment, the sensor head 426 resides at one end of the sensor 420, which is generally cylindrical. In one embodiment, the sensor head 406 includes an application surface which can include two conducting lines adjacent to each other and covered by a thin insulating film. The sensor 420 can also include promotional area 428 on the surface of a housing for the sensor 420. As an example, the promotional area 428 can carry a business logo, a trademark, or advertisement for a product or service. Although the general configuration of the sensor 420 is cylindrical, the sensor 420 can include a recessed, flattened surface 430. In this example, the display or screen 422 and the button 424 are provided at the recessed, flattened surface 430. FIG. 7C also depicts representative dimensions of the housing for the sensor 420 according to one embodiment.

FIGS. 7D and 7E are front and side views for a moisture sensor 440 according to still another embodiment of the invention. The sensor 440 also includes a display or screen 442, an on/off switch 444, and a sensor head 446. In this embodiment, the sensor head 446 resides at one end of the sensor 440, which is generally cylindrical. As shown in FIG. 7E, the sensor head 446 is angled, such that the angle 447 is an acute angle. In one embodiment, the sensor head 446 includes an application surface which can include two conducting lines adjacent to each other and covered by a thin insulating film. The sensor 440 can also include one or more promotional areas 448 on the surface of a housing for the sensor 440. As an example, the promotional area 448 can carry a business logo, a trademark, or advertisement regarding a product or service. FIG. 7E also depicts representative dimensions of the housing for the sensor 440 according to one embodiment.

FIGS. 7F, 7G and 7H are rear, side and front view for a moisture sensor 460 according to still another embodiment of the invention. The sensor 460 also includes a display or screen 462, an on/off switch 464, and a sensor head 466. In this embodiment, the sensor head 466 is placed near one end of the sensor 460, which is generally rectangular with rounded edges. In one embodiment, the sensor head 466 includes an application surface which can include two conducting lines adjacent to each other and covered by a thin insulating film. The sensor 460 can also include one or more promotional areas 468 on the surface of a housing for the sensor 460. As an example, the promotional area(s) 468 can carry a business logo, a trademark, or advertisement for a product or service. The sensor 460 can include a recessed, flattened surface 470 where the sensor head 466 is located. FIGS. 7F, 7G and 7H also depict representative dimensions of the housing for the sensor 460 according to one embodiment.

In another embodiment, the sensor 460 can be in the shape of a nail file, with a front surface and a back surface. The application surface of the sensor head can be on the front surface, at one end of the filer, while the on/off switch with the display are on the back surface. Optionally, the sensor 460 can also actually provide a nail file surface so as to serve as a nail file.

In one embodiment, the sensor includes a mechanism to allow at least one of its electrical components to be connected to an electrical component outside the sensor. For example, the sensor includes a connector, which could be a standard connector, to allow the measurements made by the sensor to be captured and analyzed by another computing device. In another example, the sensor includes a wireless transceiver to allow, for example, measurements made by the sensor to be wirelessly transmitted to another device and to be displayed by the another device. The another device could be a portable device also carried by the user and the portable device has a display. The wireless technologies could be based on Bluetooth®, WiFi or other standards.

The sensor can be incorporated into other devices. For example, the moisture sensor is incorporated into a pen, a phone, a key chain or a pair of glasses. To illustrate, the sensor is incorporated into a pen. As one writes, the pen can automatically measure the dryness of the person's skin. Similarly, the sensor can be in a phone. As one makes a phone call, the sensor can measure the dryness of the person's skin touching the sensor head on the phone.

In another embodiment, the sensor can be incorporated into a holder in the configuration of a lipstick or chapstick. For example, the sensor head is on the top surface of one end (e.g., on a base end or a cap end) of a product similar to a lipstick. There is also a display or a beeper on the lipstick. In one embodiment, based on measurements by the sensor, if a person's skin is too dry, the person can remove the cap, and apply the moisturizing materials inside, such as by rotating the bottom portion of the holder, as in a lipstick.

In one embodiment, a moisture sensor is personalized to a user, depending on the skin type of the user. Depending on whether the skin type of the user is dry/medium/moist, the user can adjust the sensor accordingly, or can acquire different types of sensors. For example, with the skin type selected, the full range of the output would be for that specific skin type. If the output is in scales of 1 through 5, the entire range would be applicable for the skin type selected. One way to select skin type is that the selection is configured to be done by the user. There can be a skin-type switch on the sensor. The general idea is to set the proper scale of the output of the sensor based on the position of the switch, which could be adjusted by the user. In another embodiment, the selection is configured not to be done by the user. There can be a jumper switch on a printed circuit inside the sensor. The manufacturer could set the switch position for different skin-type sensors.

Figure 8:
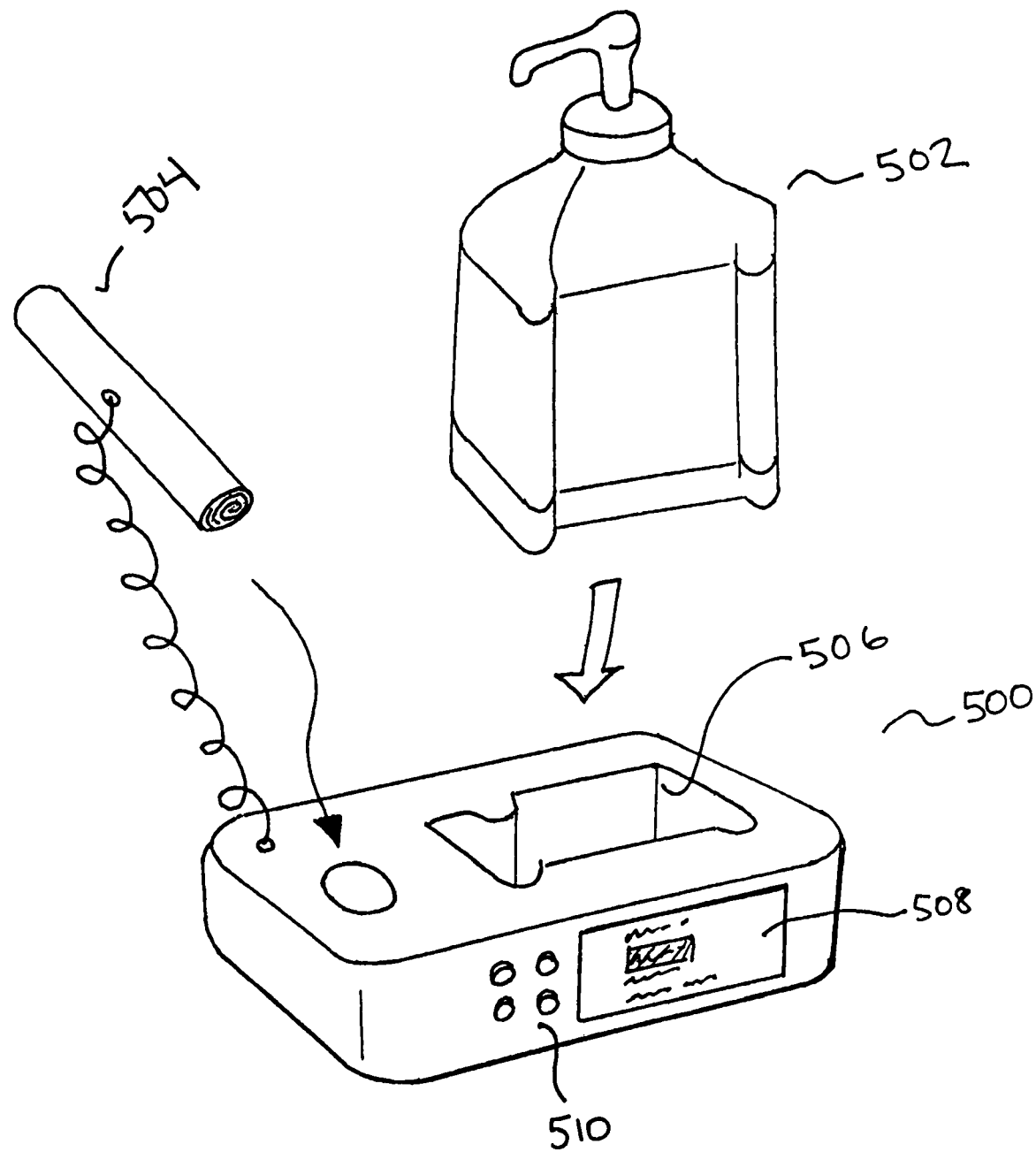
FIG. 8 shows a base for a bottle of lotion and a moisture sensor according to one embodiment of the invention.

In one embodiment, a moisture sensor and any other electrical components in the bottle are in a base that has at least one slot, opening, cavity or receptacle. FIG. 8 shows an embodiment of such a lotion base 500 with a bottle of lotion 502 and a moisture sensor 504 tethered to the base. The base 500 includes a cavity 506 for the bottle of lotion 502 to snugly fit into. The base can act like a base-station or a docking station.

In one embodiment, the base 500 includes a display 508, and a number of input switches 510, with one of them being an on/off switch. Other switches can be used for additional input mechanisms to be further described below.

In one embodiment, different brands of lotion can have its base of specific design. For example, L'OREAL® can have an L-shape base. In another example, the cavity for the lotion bottle is of a specific dimension to fit the dimension of the corresponding lotion bottles. Each brand or the lotion bottles from each company can have its own dimensions. If one is using the base from company A, the person would have to buy lotions from company A to fit into the base.

In one embodiment, there can be a standard electrical connector at the base, such as a USB connector. The connector can be used as an input/output port.

In another embodiment, when the amount of lotion in the bottle is low, the base would generate a signal. For example, the base 500 shown in FIG. 8 can include a scale that keeps track of the weight of the lotion bottle 502. As the weight goes below a certain value, a signal will be generated. The signal can be a visual signal, such as on the display 508. The signal can be audio, such as a beeping sound that is periodically produced if the weight is below the threshold. The beeping sound can be turned off, such as through one of the switches 510 shown in FIG. 8.

In yet another embodiment, the low-lotion signal is transmitted to a computer that is connected to the Internet. This can be done through a wire or a wireless connection. For example, the base can be connected to the computer through a connector at the base. In another embodiment, the base is connected to the computer wirelessly, such as to a wireless hub in its vicinity. The wireless hub, for example, can be a WiFi hub. The computer can also be wirelessly connected to the hub.

When the low-lotion signal is generated, that signal can be transmitted to the computer. Next time, when the user gets onto the computer, the user is informed that a message has arrived from his lotion bottle. After reading the message, the user is asked if he wants to send the message to a company, which can be the company selling him the lotion. Alternatively, a message regarding the low-lotion signal can be automatically sent to the company without requiring or soliciting permission from the user. The message can also ask the user if he wants the company to contact him regarding refills. If the person responds affirmatively, the person can be asked to enter his email address, and the corresponding information will be transmitted to the company.

The transmission of the messages to the company can be through the Internet. This would allow the company to become aware of the lotion usage by the person. If the person agrees to receive information from the company, such as on refills, the company can send the person a message, such as through email, asking the person if he wants a similar bottle of lotion directly sent to him. If the person answers yes, the company will mail a bottle to him, and can charge him, such as through his charge cards. In another embodiment, the person is subscribed to an automatic-lotion-refill service. Based on the service, when the company receives the low-lotion signal, the company would send the person another bottle of lotion and charges the person's credit card accordingly.

In one embodiment, a bottle of lotion can have more than one sensor. Additional sensor(s) can be used to sense one or more other parameter(s). The one or more other parameters can be related to the user of the lotion or the environment the user is in. For example, in one embodiment, a lotion bottle is for suntan lotion. The bottle includes an indicator that alerts the user to apply the lotion. The indicator can be based on dryness or moisture content of the skin. Dry skin or low moisture content can indicate the need for suntan lotion. Moderate-to-high moisture content can indicate the presence of adequate quantities of suntan lotion. In one embodiment, the moisture sensor is applied to the user before the user gets into the water. One additional sensor that can be used with the bottle is a sun sensor. The sun sensor measures radiation (e.g., light) intensity. In one embodiment, the radiation intensity can pertain to UV radiation. For example, when the measured intensity (currently or cumulatively) is beyond a certain level, the user can be alerted to apply lotion (i.e., suntan lotion), or to apply more lotion to provide the user with additional protection.

In another example, one additional sensor is a humidity sensor that provides indication as to the humidity level of the environment. In this example, recommendation to the user regarding application of lotion depends on both the user's moisture level and the humidity level of the user's environment. The lotion bottle could alert the user to apply more lotion if both the environment is dry and the user's skin is dry. In another example, if the user's skin is moist, but the environment is dry, the bottle would still recommend the user to apply lotion. Different examples of commercially available humidity sensor are applicable, such as those in packaging applicable to printed circuit board assembly process. An example of such a packaging is surface mount packages.

The one or more additional sensors can be integrated together, or integral with a lotion bottle, or a lotion base. In another embodiment, the one or more additional sensors are attached to, or integral with a moisture sensor, which is not electrically coupled to a lotion bottle, or a lotion base.

In yet another embodiment, information from one or more additional sensors is remotely measured, and then transmitted to be used with measurements from a moisture sensor. For example, a bottle of lotion is wirelessly linked to a computer, which is connected to the Internet. Through the Internet, the computer receives information regarding the general humidity level of the town the user is at. The computer passes such humidity level data to the bottle. Based on such humidity level information and measurements from a moisture sensor, the bottle provides recommendation to the user regarding lotion usage.

A number of embodiments have been described where the lotion is contained in a bottle. In one embodiment, a bottle is defined as a container or a receptacle that has a narrow neck. In another embodiment, a bottle is defined as a container or a receptacle with a width that is not uniform (some part narrower than another part, such a neck portion being narrower).

In another embodiment, a bottle does not have to have a narrow neck and a bottle can have uniform width or substantially uniform width, but the bottle has an opening or a mouth that can be plugged, corked or capped.

In yet another embodiment, lotion was bought through an online store. The online store or web-store can keep track of the fact that a user bought a specific type of lotion. Next time, when the user visits the web-store, the user can be notified of information related to similar lotion or similar skin care product. For example, if the store has a similar type of lotion that is on sale, the store can let the user know.

Different embodiments described are applicable to human beings. In one embodiment, the lotion bottle and/or the moisture sensor and/or the lotion base is applicable to animals.

A number of embodiments have been described regarding a lotion bottle and a moisture sensor. In one embodiment, instead of a bottle, different aspects described in this application are also applicable to other types of containers, such as a box. One example of such a container is a tube. The tube can be squeezed to bring out the substance the tube carries. The container can have a sensor that is integral with, or attachable to and detachable from, the container. The sensor can be configured to measure an attribute of a living being with the container containing a substance that affects the attribute. The sensor and the container together as a unit can be portable.

The discussion above often refers to lotion, or more generally skin care products, for skin. Another embodiment of the invention pertains to hair care products for one's scalp. In one embodiment, the scalp can be considered skin on a person's head, and the hair care products can be considered skin care products. A sensor can measure an attribute of the scalp to determine if hair care products are needed, such as the type of shampoo. For example, a moisture sensor could measure the dryness of the scalp of the user. A scalp with a lot of dandruff has little moisture, and can benefit from specific shampoo for people with a lot of dandruff. Hence, the moisture sensor measurements can identify a specific hair care product or a class of hair care products, such as a type of shampoo.

Figure 9:
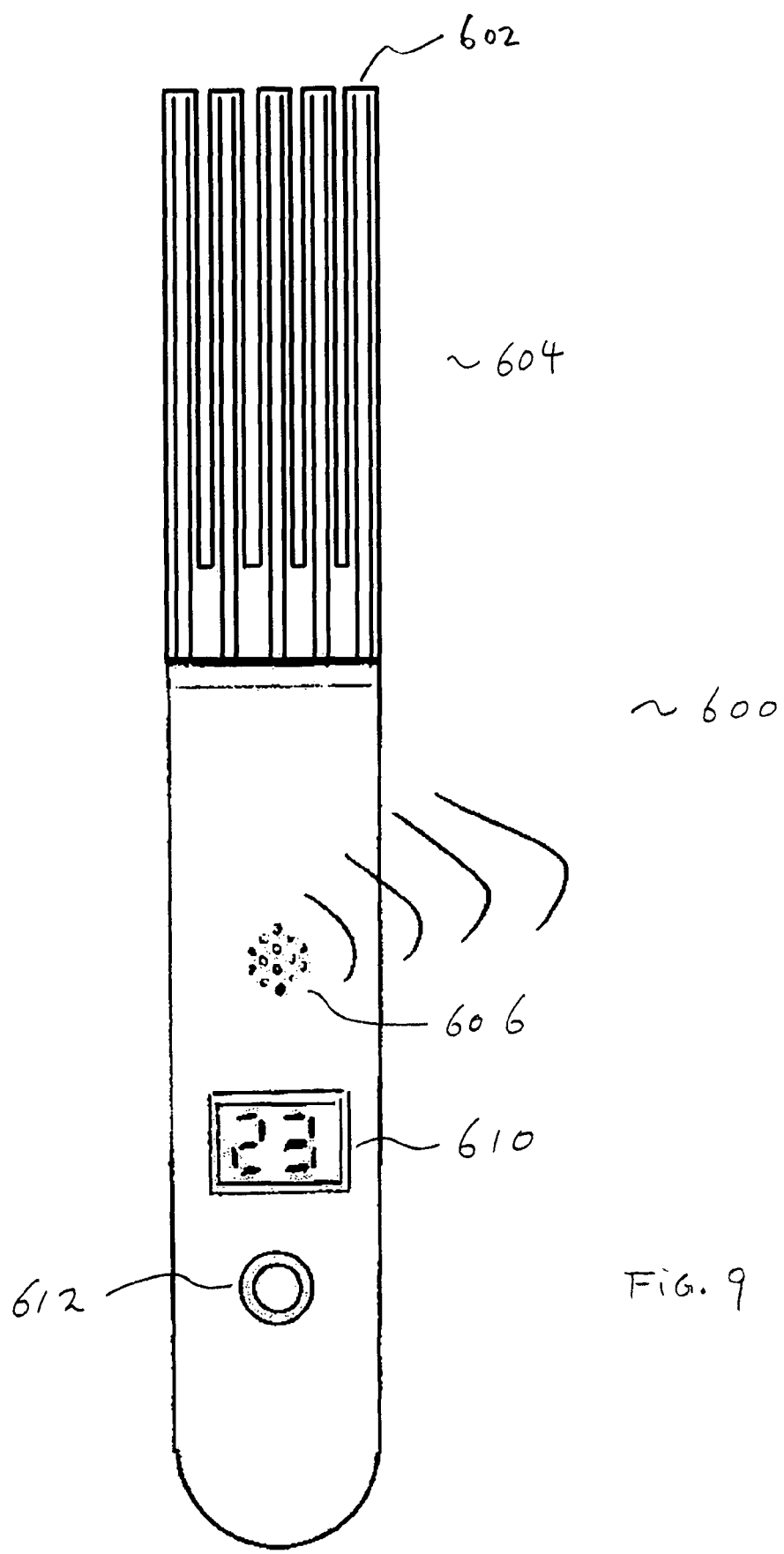
FIG. 9 shows one embodiment of a moisture sensor for measuring the scalp according to the invention.

FIG. 9 shows one embodiment of a moisture sensor 600 for the scalp. The sensor head 604 includes a number of narrow strips, probes or fingers 602. In this example, the sensor also could include a speaker 606, a display 610 and a switch 612. The speaker 606 could provide indications as to when measurements are done. The display 610 could display the measurements, while the switch 612 could be an on/off switch. Each finger has at least two conducting lines closely-spaced adjacent to each other, with the lines covered by a thin piece of insulating material, for capacitance measurement. As an example, each line can be 7 mils wide and the spacing between lines can be also 7 mils or other dimensions. In FIG. 9, only two conducting lines are shown in each finger. The lines as shown serve as illustrations. In different embodiments, there could be a number of lines adjacent to each other similar, for example, to those shown in FIG. 1C. In one embodiment, the width of each strip or finger is about 0.05", with about 0.05" spacing between strips. The narrow fingers improve the ease of having the sensor head touch the scalp when the scalp is covered by a layer of hair. For example, the narrow fingers allow placing the sensor strips directly against the scalp, in between and under the hairs.

Figure 10:
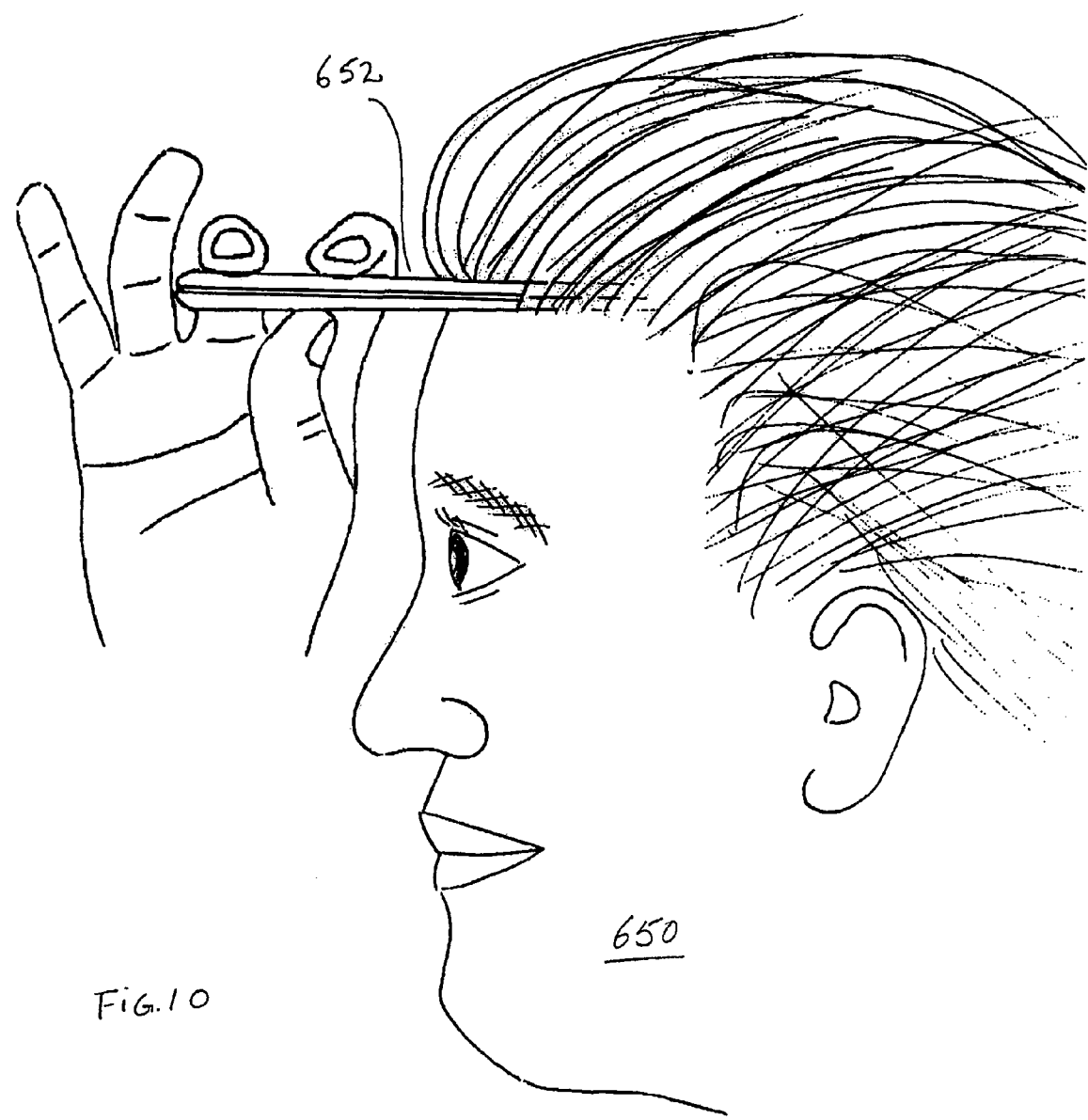
FIG. 10 shows an example of a user using a moisture sensor for the scalp according to the invention.

FIG. 10 shows an example of a user 650 using a moisture sensor for the scalp 652, such as the one shown in FIG. 9. The user 650 places the strips into the hair, and presses them onto his scalp. Then the user activates the on/off switch to start measuring. When the measurement is done, the sensor 652 produces an audible signal to alert the user. The multiple fingers increase the intensity level and accuracy of the measured signals. In the example shown in FIG. 9, capacitances measured by each pair of conducting lines are added in parallel to increase the signal level.

In one embodiment, the multiple narrow fingers are in the shape of a comb, and circuits on all of the strips could be on the same printed circuit board. As an example, there are sixteen fingers per inch, each finger being about 0.03125" wide, with about 0.03125" spacing between each pair of fingers.

A number of embodiments have been described regarding a moisture sensor that includes at least two conducting lines adjacent to each other, with the lines covered by a thin piece of insulating material, for capacitance measurement. In another embodiment, the moisture sensing mechanism is based on Raman spectroscopy using infrared technologies. For example, the sensor head includes a near-infrared emitter and a near-infrared detector. With the sensor head applied to an area of skin, a portion of the emitted infrared radiation is reflected by the skin and absorbed by the detector. The detector includes a filter to measure specific spectral frequency bands. Based on the intensity measured, the sensor head determines the amount of moisture level in the area of skin. In one embodiment, such a sensor is used to measure the moisture level of the scalp of a person. Since the emitter and detector could occupy a relatively small area, the sensor head could be relatively small. In one embodiment, there are more than one probe or fingers as in FIG. 9, with an emitter/detector pair on each finger. Multiple pairs provide redundancy in the output data and could improve measurement accuracy.

In another embodiment, a moisture sensor head includes both conducting lines adjacent to each other for capacitance measurements, and one or more near-infrared emitter/detector pair for infrared measurements. In one embodiment, the two types of moisture sensors focus on measuring moisture level at different layers of the skin below the skin surface.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Also, in this specification, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A handheld moisture sensor for the skin of a user, comprising:
   a sensor head on a circuit board configured to provide an indication regarding skin moisture level of the user by applying the sensor head on the skin of the user;
   an output device connected to the circuit board;
   an electronic controller on the circuit board, the controller being configured or designed to at least generate an output for the output device based on the indication from the circuit board; and
   a power source connected to the circuit board to provide power at least to the controller and the output device,
   wherein the moisture sensor provides a piece of information regarding the application of a skin-care product to the skin of the user, and
   wherein the sensor head includes a plurality of fingers and each finger has at least two conducting lines adjacent to each other, with the lines covered by an insulating material, and wherein the sensor head measures capacitance during operation.

2. A handheld moisture sensor as recited in claim 1, wherein the plurality of fingers as a whole are in a configuration similar to a comb.

3. A handheld moisture sensor as recited in claim 1,
   wherein the skin is the scalp of the user, and
   wherein the skin-care product is a conditioner.

4. A handheld moisture sensor as recited in claim 1 wherein the skin-care product is lotion.

5. A handheld moisture sensor as recited in claim 1 wherein at least one electrical component in the sensor is electrically coupled to at least one electrical component in a bottle.

6. A handheld moisture sensor as recited in claim 1 wherein the output device includes a display.

7. A handheld moisture sensor as recited in claim 6, wherein the display displays an advertisement.

8. A handheld moisture sensor as recited in claim 1 wherein the output device includes a speaker.

9. A handheld moisture sensor as recited in claim 1
   wherein the circuit board is a flexible circuit board to allow the sensor head to better conform to the curvature of the skin surface being measured.

10. A handheld moisture sensor as recited in claim 1 wherein the sensor includes an electrical connector.

11. A handheld moisture sensor as recited in claim 1 wherein the sensor includes a wireless transmitter.

12. A handheld moisture sensor as recited in claim 1 wherein the output device provides an indication when the skin measurement is accomplished.

13. A handheld moisture sensor as recited in claim 1 wherein the sensor head includes a constant force mechanism, which is configured to maintain a constant force when the sensor head is applied or pressed onto the surface to be measured.

14. A handheld moisture sensor as recited in claim 1 wherein the sensor includes a plurality of settings, each for one type of skin to allow the sensor to be personalized to the skin type of the user.

15. A handheld moisture sensor as recited in claim 1,
    wherein the skin is the scalp of the user, and
    wherein the skin-care product is shampoo.

16. A handheld moisture sensor as recited in claim 6, wherein the sensor includes a wireless transmitter.

17. A handheld moisture sensor as recited in claim 1 wherein the sensor provides a recommendation to the user regarding the user's skin based on the measurements by the sensor and based on another piece of information from an additional sensor, which measures an attribute different from an attribute regarding skin moisture level measured by the sensor head.

18. A handheld moisture sensor as recited in claim 17, wherein the additional sensor is a humidity sensor.

19. A handheld moisture sensor as recited in claim 1, wherein at least a portion of the circuit board is flexible to allow the sensor head to better conform to the curvature of the skin surface being measured.

20. A handheld moisture sensor as recited in claim 19 wherein the sensor includes a wireless transmitter.

* * * * *

UNITED STATES PATENT AND TRADEMARK OFFICE
CERTIFICATE OF CORRECTION

Page 1 of 1

PATENT NO. : 8,118,740 B2
APPLICATION NO. : 11/479665
DATED : February 21, 2012
INVENTOR(S) : Howell et al.

It is certified that error appears in the above-identified patent and that said Letters Patent is hereby corrected as shown below:

Title Page, item (56),

On Page 2, under Other Publications
On the right column, "ViOptix, Technology Overview, copyright 2006, VIOptix, Inc., http://www.vioptix.com/docs/technology/technology.asp., downloaded Dec. 5, 2006, pp.1." should be --ViOptix, Technology Overview, copyright 2006, ViOptix, Inc., http://www.vioptix.com/docs/technology/technology.asp., downloaded Dec. 5, 3006, one page.--.

On the right column, "Etude, "The Way to skin counseling" Operation Manual, 2005. front cover page and pp. 1-27."
should be --étude, "The Way to skin counseling" Operation Manual, 2005, front cover page and pp. 1-27.--.

On the right column, "LifePoInt Inc.—Saliva Based Testing Systems for the next generation, LifePoint ® IMPACT ®Test System, downloaded 2005, 2 pages."
should be --LifePoint Inc.—Saliva Based Testing Systems for the next generation, LifePoint ® IMPACT ®Test System, downloaded 2005, 2 pages.--.

In the Specification
On Column 6, line 9, "On the embodiment that the sensor is not tethered" should be --In the embodiment that the sensor is not tethered--.

Signed and Sealed this
Twenty-first Day of April, 2015

Michelle K. Lee
*Director of the United States Patent and Trademark Office*